(12) United States Patent
Hollingshead et al.

(10) Patent No.: US 9,399,078 B2
(45) Date of Patent: Jul. 26, 2016

(54) UNSCENTED AND LOW SCENTED MALODOR CONTROL COMPOSITIONS AND METHODS THEREOF

(75) Inventors: Judith Ann Hollingshead, Batavia, OH (US); Steven Anthony Horenziak, Cincinnati, OH (US); Zaiyou Liu, West Chester, OH (US); Michael-Vincent Nario Malanyaon, Indian Springs, OH (US); Christine Marie Readnour, Ft. Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 1251 days.

(21) Appl. No.: 13/249,616

(22) Filed: Sep. 30, 2011

(65) Prior Publication Data

US 2013/0085204 A1    Apr. 4, 2013

(51) Int. Cl.
*A61L 9/01*      (2006.01)
*C11B 9/00*      (2006.01)
*B65F 1/00*      (2006.01)

(52) U.S. Cl.
CPC .................. *A61L 9/01* (2013.01); *B65F 1/0026* (2013.01); *C11B 9/0015* (2013.01); *C11B 9/0019* (2013.01); *C11B 9/0049* (2013.01); *C11B 9/0061* (2013.01)

(58) Field of Classification Search
CPC ....................................................... A61L 9/01
USPC ....................................................... 523/102
See application file for complete search history.

(56) References Cited

U.S. PATENT DOCUMENTS

| | | | |
|---|---|---|---|
| 3,745,131 A | | 7/1973 | Jaggers et al. |
| 3,917,870 A | * | 11/1975 | Slangan et al. ............... 426/535 |
| 4,359,395 A | | 11/1982 | Schreck et al. |
| 4,515,909 A | | 5/1985 | Sawano et al. |
| 4,582,635 A | | 4/1986 | Furuuchi et al. |
| 5,711,941 A | | 1/1998 | Behan et al. |
| 5,849,310 A | | 12/1998 | Trinh et al. |
| 6,086,903 A | | 7/2000 | Trinh et al. |
| 6,180,121 B1 | | 1/2001 | Guenin et al. |
| 6,475,473 B1 | | 11/2002 | Perring et al. |
| 6,921,581 B2 | | 7/2005 | Van Gelder et al. |
| 7,833,515 B2 | | 11/2010 | Corzani et al. |
| 7,884,063 B2 | | 2/2011 | Striepling et al. |
| 8,357,359 B2 | | 1/2013 | Woo et al. |
| 8,404,630 B2 | | 3/2013 | Gambogi et al. |
| 2001/0056080 A1 | | 12/2001 | Woo et al. |
| 2002/0132070 A1 | | 9/2002 | Franzen et al. |
| 2003/0191034 A1 | | 10/2003 | Woo et al. |
| 2004/0115091 A1 | | 6/2004 | Beerling et al. |
| 2007/0149639 A1 | | 6/2007 | Horikoshi et al. |
| 2007/0185228 A1 | | 8/2007 | Dente et al. |
| 2008/0009560 A1 | | 1/2008 | McKay, Jr. |
| 2008/0207476 A1 | | 8/2008 | Artiga et al. |
| 2008/0207481 A1 | | 8/2008 | Meine et al. |
| 2008/0221003 A1 | | 9/2008 | Meine et al. |
| 2009/0067760 A1 | | 3/2009 | Shelley et al. |
| 2009/0087401 A1 | | 4/2009 | Hiramoto et al. |
| 2009/0202599 A1 | | 8/2009 | Zhou et al. |
| 2009/0257973 A1 | | 10/2009 | Fraser et al. |
| 2009/0269297 A1 | | 10/2009 | Conover |
| 2009/0326093 A1 | | 12/2009 | Funk et al. |
| 2010/0047198 A1 | * | 2/2010 | Striepling et al. ............... 424/59 |
| 2010/0111889 A1 | | 5/2010 | Marsh et al. |
| 2010/0115708 A1 | * | 5/2010 | Caswell et al. ................... 8/137 |
| 2010/0187135 A1 | | 7/2010 | Broering et al. |
| 2010/0287710 A1 | | 11/2010 | Denutte et al. |
| 2011/0150815 A1 | * | 6/2011 | Woo et al. ..................... 424/76.2 |
| 2013/0266642 A1 | | 10/2013 | Hollingshead et al. |

FOREIGN PATENT DOCUMENTS

| | | |
|---|---|---|
| DE | 102007021796 A1 | 11/2008 |
| GB | 2 422 780 A | 8/2006 |
| JP | 2001081669 | 3/2001 |
| JP | 2002-327193 A1 | 11/2002 |
| JP | A-2002-327193 A | 11/2002 |
| JP | 2005015686 | 1/2005 |
| JP | A-2005-029753 | 2/2005 |
| KR | 100623932 B1 | 9/2006 |
| KR | 20080096995 | 11/2008 |
| WO | WO 2008/129028 A1 | 10/2008 |
| WO | WO 2009/107814 A1 | 9/2009 |
| WO | WO 2007/107856 A1 | 10/2009 |
| WO | WO 2012/078626 A2 | 6/2012 |

OTHER PUBLICATIONS

PCT Search Report for application No. PCT/US/2011/063525, dated Jul. 13, 2012, containing 18 pages.

* cited by examiner

*Primary Examiner* — Michael Pepitone
(74) *Attorney, Agent, or Firm* — Abbey A. Lopez; Amy I. Ahn-Roll

(57) ABSTRACT

Unscented and low scented malodor control compositions are provided. The malodor control compositions are suitable for a variety of applications, including use on plastic films or in fabric and air freshening products.

19 Claims, 2 Drawing Sheets

UNSCENTED AND LOW SCENTED MALODOR CONTROL COMPOSITIONS AND METHODS THEREOF

CROSS-REFERENCES TO RELATED APPLICATIONS

This application claims the benefit under 35 U.S.C. §120 to U.S. application Ser. No. 12/962,691 filed Dec. 8, 2010 which claims priority under 35 U.S.C. §119(e) to U.S. Provisional Application Ser. No. 61/287,369 filed Dec. 17, 2009.

FIELD OF THE INVENTION

The present invention relates to unscented and low scented malodor control compositions and methods thereof. The malodor control compositions are suitable for use in a variety of applications, including use in air freshening composition and on plastic films for garbage bags.

BACKGROUND OF THE INVENTION

Products for controlling malodors are well known in the art and are widely described in patent literature. These products may be designed to work specifically in air, on fabrics, or with plastic films. See, e.g., U.S. Patent Publication Nos. 2009/0326093 and 2009/0067760.

Unscented or low scented products are desired by consumers as they may be considered more natural and discreet to use than scented products. Manufacturers of unscented or low scented products for controlling malodors rely on malodor control ingredients or other technologies (e.g. filters) to reduce malodors. However, effectively controlling both amine-based malodors (e.g fish and urine) and sulfur-based malodors (e.g. garlic and onion) may be difficult, and the time required for a product to noticeably reduce malodors may create consumer doubt as to the product's efficacy on malodors. Often times, manufacturers incorporate scented perfumes to help mask these difficult malodors.

There remains a need for unscented and low scent malodor control compositions that controls a broad range of malodors.

SUMMARY OF THE INVENTION

In one embodiment, there is provided a malodor control composition comprising a perfume mixture comprising an effective amount of benzophenone, methyl palmitate, farnesol, vetivert acetate, and undecylenic aldehyde for reducing malodors.

In another embodiment, there is provided a malodor control composition comprising a perfume mixture comprising about 30% to about 100%, by weight of said perfume mixture, of benzophenone, methyl palmitate, farnesol, and mixtures thereof.

In yet another embodiment, there is provided a plastic film comprising a perfume mixture comprising an effective amount of at least 2 perfume ingredients selected from the group consisting of: benzophenone, undecylenic aldehyde, methyl palmitate, vetivert acetate, farnesol, and mixtures thereof, wherein said perfume mixture reduces malodors in the air.

In yet another embodiment, there is provided a malodor control composition comprising a perfume mixture comprising styrax coeur and an effective amount of at least one perfume material selected from the group consisting of: benzophenone, undecylenic aldehyde, methyl palmitate, vetivert acetate, farnesol, and mixtures thereof, wherein said perfume mixture reduces malodors.

In yet another embodiment, there is provided a method of controlling malodors and providing a low scent composition via providing a malodor control composition comprising a perfume mixture comprising an effective amount of benzophenone, methyl palmitate, farnesol, vetivert acetate, and undecylenic aldehyde; and contacting the malodor control composition with a malodor.

DETAILED DESCRIPTION OF THE INVENTION

Figure 1:
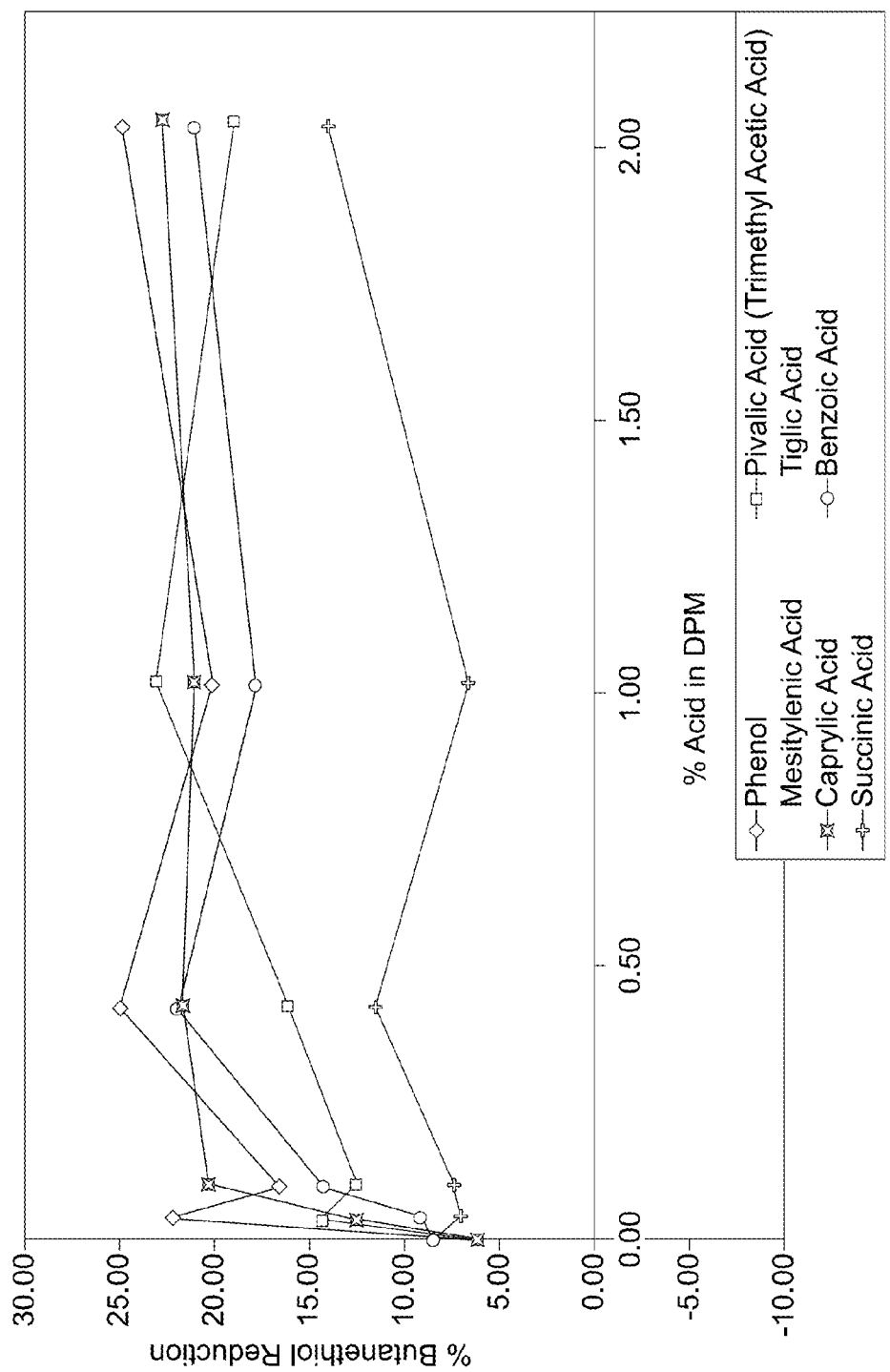
FIG. 1 is a graph showing butanethiol reduction by thiophene carboxaldehyde in combination with various acid catalysts.

The present invention relates to unscented and low scented malodor control composition and methods thereof. Unscented and low scented malodor control compositions of the present invention comprise perfume mixtures that are substantially free of scent yet control malodors through odor neutralization and odor blocking technologies. The perceptible perfume scent intensity and malodor efficacy of a composition can be determined using the tests outlined herein.

"Malodor" refers to compounds generally offensive or unpleasant to most people, such as the complex odors associated with bowel movements.

"Neutralize" or "neutralization" refers to the ability of a compound or product to reduce or eliminate malodorous compounds. Odor neutralization may be partial, affecting only some of the malodorous compounds in a given context, or affecting only part of a malodorous compound. A malodorous compound may be neutralized by chemical reaction resulting in a new chemical entity, by sequestration, by chelation, by association, or by any other interaction rendering the malodorous compound less malodorous or non-malodorous. Neutralization is distinguishable from odor masking or odor blocking by a change in the malodorous compound, as opposed to a change in the ability to perceive the malodor without any corresponding change in the condition of the malodorous compound. Malodor neutralization provides a sensory and analytically measurable (e.g. gas chromatograph) malodor reduction. Thus, if a malodor control composition delivers genuine malodor neutralization, the composition will reduce malodors in the vapor and/or liquid phase.

"Odor blocking" refers to the ability of a compound to dull the human sense of smell.

"Odor masking" refers to the ability of a compound with a non-offensive or pleasant smell that is dosed such that it limits the ability to sense a malodorous compound. Odor-masking may involve the selection of compounds which coordinate with an anticipated malodor to change the perception of the overall scent provided by the combination of odorous compounds.

I. Malodor Control Compositions

The malodor control compositions of the present invention include an unscented or low scented perfume mixture designed to control malodors by neutralization and blocking and not function merely by covering up or masking odors. The malodor control composition may also include an acid catalyst for more quickly neutralizing malodors and other optional ingredients for particular applications.

1. Unscented and Low Scented Perfume Mixture

The malodor control compositions of the present invention may include an unscented or low scented mixture of perfume materials that neutralize and block malodors. In some embodiments, the unscented or low scented perfume mixture may include benzophenone, farnesol, undecylenic aldehyde, and mixtures thereof.

Suitable perfume materials may have a vapor pressure (VP) in the range of about 0.0001 torr to 100 torr, alternatively about 0.0001 torr to about 10 torr, alternatively about 0.0001 torr to about 0.100 torr, alternatively about 0.001 torr to about 50 torr, alternatively about 0.001 torr to about 20 torr, alternatively about 0.001 torr to about 0.100 torr, alternatively about 0.001 torr to 0.06 torr, alternatively about 0.001 torr to 0.03 torr, alternatively about 0.005 torr to about 20 torr, alternatively about 0.005 torr to about 0.100 torr, alternatively about 0.01 torr to about 20 torr, alternatively about 0.01 torr to about 15 torr, alternatively about 0.01 torr to about 10 torr, alternatively about 0.05 torr to about 10 torr, measured at 25° C.

The perfume materials of the present invention may be defined by their boiling point (B.P.) and octanol/water partition coefficient (P). The boiling point referred to herein is measured under normal standard pressure of 760 mmHg The boiling points of many perfume materials, at standard 760 mm Hg, are outlined in "Perfume and Flavor Chemicals (Aroma Chemicals)," written and published by Steffen Arctander, 1969.

The octanol/water partition coefficient of a perfume material is the ratio between its equilibrium concentrations in octanol and in water. The partition coefficients of the perfume material used in the malodor control composition may more conveniently be given in the form of their logarithm to the base 10, log P. The log P values of many perfume materials have been reported. See, e.g., the Pomona 92 database, available from Daylight Chemical Information Systems, Inc. (Daylight CIS), Irvine, Calif. However, the log P values are most conveniently calculated by the Biobyte C log P program contained in Daylight Software version 4.94, also available for license from Daylight CIS. This program also lists experimental log P values when they are available in the Pomona92 database. The "calculated log P" (C log P) is determined by the fragment approach of Hansch and Leo (cf, A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume material, and takes into account the numbers and types of atoms, the atom connectivity, and chemical bonding. The C log P values, which are the most reliable and widely used estimates for this physicochemical property, are preferably used instead of the experimental log P values in the selection of perfume materials for the malodor control composition. The C log P values may be defined by four groups and the perfume materials may be selected from one or more of these groups. The first group comprises volatile aldehydes that have a B.P. of about 250° C. or less and C log P of about 3 or less. The second group comprises volatile aldehydes that have a B.P. of 250° C. or less and C log P of 3.0 or more. The third group comprises volatile aldehydes that have a B.P. of 250° C. or more and C log P of 3.0 or less. The fourth group comprises volatile aldehydes that have a B.P. of 250° C. or more and C log P of 3.0 or more. The malodor control composition may comprise any combination of volatile aldehydes from one or more of the C log P groups.

Suitable perfume materials include Benzophenone, Methyl Palmitate, Farnesol, Vetivert Acetate, Cedryl Methyl Ether, Vertofix Couer (methyl cedrylone), and mixtures thereof. Suitable perfume materials may also include Helional (alpha-methyl-3,4-(methylenedioxy)-hydrocinnamaldehyde), Florhydral, Undecylenic Aldehyde, Adoxal (2,6,10-Trimethyl-9-undecenal), Bourgeonal (4-t-butylbenzenepropionaldehyde), Cymal, Florhydral (3-(3-isopropylphenyl)-butyraldehyde), Citronellal (3,7-dimethyl 6-octenal), Floralozone (para-ethyl-alpha,alpha-dimethyl hydrocinnamaldehyde), Floral Super, Pino Acetaldehyde, Styrax Coeur.

Suitable perfume materials may also include volatile aldehydes or reactive aldehydes (RA) including, but are not limited to, Lilestralis 33 (2-methyl-4-t-butylphenyl)propanal), Cinnamic aldehyde, cinnamaldehyde (phenyl propenal, 3-phenyl-2-propenal), Citral, Geranial, Neral (dimethyloctadienal, 3,7-dimethyl-2,6-octadien-1-al), Cyclal C (2,4-dimethyl-3, -cyclohexen-1-carbaldehyde), cyclamen aldehyde, Cyclosal, Lime aldehyde (Alpha-methyl-p-isopropyl phenyl propyl aldehyde), Methyl Nonyl Acetaldehyde, aldehyde C12 MNA (2-methyl-1-undecanal), Hydroxycitronellal, citronellal hydrate (7-hydroxy-3,7-dimethyl octan-1-al), hydrocinnamaldehyde (3-phenylpropanal, 3-phenylpropionaldehyde), Intreleven aldehyde (undec-10-en-1-al), Ligustral, Trivertal (2,4-dimethyl-3-cyclohexene-1-carboxaldehyde), Jasmorange, satinaldehyde (2-methyl-3-tolylproionaldehyde, 4-dimethylbenzenepropanal), Lyral (4-(4-hydroxy-4-methyl pentyl)-3-cyclohexene-1-carboxaldehyde), Melonal (2,6-Dimethyl-5, -Heptenal), Methoxy Melonal (6-methoxy-2,6-dimethylheptanal), methoxycinnamaldehyde (trans-4-methoxycinnamaldehyde), Myrac aldehyde isohexenyl cyclohexenyl-carboxaldehyde, trifernal ((3-methyl-4-phenyl propanal, 3-phenyl butanal), lilial, P.T. Bucinal, lysmeral, benzenepropanal (4-tert-butyl-alpha-methyl-hydrocinnamaldehyde), Dupic al, tricyclodecylidenebutanal (4-Tricyclo5210-2,6decylidene-8butanal), Melafleur (1,2,3,4,5,6,7,8,-octahydro-8,8-dimethyl-2-naphthaldehyde), Methyl Octyl Acetaldehyde, aldehyde C-11 MOA (2-methyl deca-1-al), Onicidal (2,6,10-trimethyl-5,9-undec adien-1-al), Muguet aldehyde 50 (3,7, -dimethyl-6-octenyl)oxyacetaldehyde), phenylacetaldehyde, Mefranal (3-methyl-5-phenyl pentanal), Triplal, Vertocitral dimethyl tetrahydrobenzene aldehyde (2,4-dimethyl-3, -cyclohexene-1-carboxaldehyde), 2-phenylproprionaldehyde, Hydrotrop aldehyde, Canthoxal, anisylpropanal 4-methoxy-alpha-methyl benzenepropanal (2-anisylidene propanal), Cylcemone A (1,2,3,4,5,6,7,8-octahydro-8,8-dimethyl-2-naphthaldehyde), and Precylcemone B (1, -cyclohexene-1-carboxaldehyde).

Suitable volatile aldehydes may also include acetaldehyde (ethanal), pentanal, valeraldehyde, amylaldehyde, Scentenal (octahydro-5-methoxy-4,7-Methano-1H-indene-2, -carboxaldehyde), propionaldehyde (propanal), Cyclocitral, beta-cyclocitral, (2,6,6-trimethyl-1, -cyclohexene-1-acetaldehyde), Iso Cyclocitral (2,4,6-trimethyl-3-cyclohexene-1-carboxaldehyde), isobutyraldehyde, butyraldehyde, isovaleraldehyde (3-methyl butyraldehyde), methylbutyraldehyde (2-methyl butyraldehyde, 2-methyl butanal), Dihydrocitronellal (3,7, -dimethyl octan-1-al), 2-Ethylbutyraldehyde, 3-Methyl-2-butenal, 2-Methylpentanal, 2-Methyl Valeraldehyde, Hexenal (2-hexenal, trans-2-hexenal), Heptanal, Octanal, Nonanal, Decanal, Tridecanal, 2-Dodecanal, Methylthiobutanal, Glutaraldehyde, Pentanedial, Glutaric aldehyde, Heptenal, cis or trans-Heptenal, Undecenal (2-, 10-), 2,4-octadienal, Nonenal (2-, 6-), Decenal (2-, 4-), 2,4-hexadienal, 2,4-Decadienal, 2,6-Nonadienal, Octenal, 2,6-dimethyl 5-heptenal, 2, -isopropyl-5-methyl-2-hexenal, Trifernal, beta methyl Benzenepropanal, 2,6,6-Trimethyl-1, -cyclohexene-1-acetaldehyde, phenyl Butenal (2-phenyl 2-butenal), 2.Methyl-3(p-isopropylphenyl)-propionaldehyde, 3-(p-isopropylphenyl)-propionaldehyde, p-Tolylacetaldehyde (4-methylphenylacetaldehyde), Anis aldehyde (p-methoxybenzene aldehyde), Benzaldehyde, Vernaldehyde (1-Methyl-4-(4-methylpentyl)-3-cyclohexenecarbaldehyde), Heliotropin (piperonal) 3,4-Methylene dioxy benzaldehyde, alpha-Amylcinnamic aldehyde, 2-pentyl-3, -phenylpropenoic aldehyde, Vanillin (4-methoxy 3-hydroxy benzaldehyde), Ethyl vanillin (3, -ethoxy 4-hydroxybenzaldehyde), Hexyl Cinnamic aldehyde, Jasmonal H (alpha-n-hexyl-cinnamaldehyde), Acalea (p-methyl-alpha-pentylcinnamaldehyde), methylcinnamaldehyde, alpha-Methylcinnamaldehyde (2-methyl 3-pheny propenal), alpha-hexylcinnamaldehyde (2, -hexyl 3-phenyl propenal), Salicylaldehyde (2-hydroxy benzaldehyde), 4-ethyl benzaldehyde, Cuminaldehyde (4-isopropyl benzaldehyde), Ethoxybenzaldehyde, 2,4-dimethylbenzaldehyde, Veratraldehyde (3,4-dimethoxybenzaldehyde), Syringaldehyde (3,5-dimethoxy 4, -hydroxybenzaldehyde), Catechaldehyde (3,4-dihydroxybenzaldehyde), Safranal (2,6,6-trimethyl-1,3-diene methanal), Myrtenal (pin-2-ene-1-carbaldehyde), Perillaldehyde L-4(1-methylethenyl)-1-cyclohexene-1-carboxaldehyde), 2,4-Dimethyl-3-cyclohexene carboxaldehyde, 2-Methyl-2, -pentenal, 2-methylpentenal, pyruvaldehyde, formyl Tricyclodecan, Mandarin aldehyde, Cyclemax, Corps Iris, Maceal, and Corps 4322.

Aldehydes that are partially volatile may be considered a volatile aldehyde as used herein.

In some embodiments, the malodor control composition includes fast reacting volatile aldehydes. "Fast reacting volatile aldehydes" refers to volatile aldehydes that either (1) reduce amine odors by 20% or more in less than 40 seconds; or (2) reduce thiol odors by 20% or more in less than 30 minutes. Fast reacting volatile aldehydes can be identified by the method outlined in the Example outlined herein, titled "Analytical Test—Effect of volatile aldehydes on amine-based and sulfur-based malodors".

The unscented or low scented perfume mixture may comprise from about 30% to about 100%, by weight of said perfume mixture, of benzophenone, methyl palmitate, farnesol, and mixtures thereof. Alternatively, the perfume mixture may comprise about 35% to about 95%, alternatively about 40%, alternatively about 80%, alternatively about 90%, by weight of said perfume mixture, of benzophenone, methyl palmitate, farnesol, and mixtures thereof.

Table 1 shows one embodiment of a perfume mixture suitable for the malodor control composition of the present invention.

TABLE 1

Low Scent Mixture

| Perfume Material | CAS Number | Wt. % (by weight of the perfume mixture) |
|---|---|---|
| Floral Super | 71077-31-1 | 1 |
| Undecylenic Aldehyde | 112-45-8 | 0.5 |
| Pino Acetaldehyde | 33885-51-7 | 1 |
| Cedryl Methyl Ether | 19870-74-7 | 1 |
| Florhydral | 125109-85-5 | 10 |
| Cymal | 103-95-7 | 3 |
| Adoxal | 141-13-9 | 1 |
| Floralozone | 67634-14-4 | 12 |
| Bourgeonal | 18127-01-0 | 1.5 |
| Benzophenone | 119-61-9 | 20 |
| Vertofix Coeur | 32388-55-9 | 10 |

TABLE 1-continued

Low Scent Mixture

| Perfume Material | CAS Number | Wt. % (by weight of the perfume mixture) |
|---|---|---|
| Helional | 1205-17-0 | 15 |
| Methyl Palmitate | 112-39-0 | 4.8 |
| Vetivert Acetate | 68917-34-0 | 0.2 |
| Farnesol | 4602-84-0 | 15 |
| Flor Acetate | 2500-83-6 | 4 |

Table 2 shows another embodiment of a perfume mixture suitable for the malodor control composition of the present invention.

TABLE 2

Unscented Mixture

| Perfume Material | CAS_Number | Wt. % (by weight of the perfume mixture) |
|---|---|---|
| Undecylenic Aldehyde | 112-45-8 | 0.200 |
| Cedryl Methyl Ether | 19870-74-7 | 0.500 |
| Florhydral | 125109-85-5 | 1.000 |
| Adoxal | 141-13-9 | 1.000 |
| Benzophenone | 119-61-9 | 27.000 |
| Vertofix Coeur | 32388-55-9 | 3.800 |
| Helional | 1205-17-0 | 1.000 |
| Methyl Palmitate | 112-39-0 | 25.000 |
| Vetivert Acetate | 117-98-6 | 0.500 |
| Farnesol | 4602-84-0 | 40.000 |

Table 3 shows yet another embodiment of a perfume mixture suitable for the malodor control composition of the present invention.

TABLE 3

Plastic Low Scented Mixture

| Perfume Material | CAS_Number | Wt. % (by weight of the perfume mixture) |
|---|---|---|
| Undecylenic Aldehyde | 112-45-8 | 0.100 |
| Cedryl Methyl Ether | 19870-74-7 | 0.500 |
| Florhydral | 125109-85-5 | 1.500 |
| Floralozone | 67634-14-4 | 0.400 |
| Bourgeonal | 18127-01-0 | 1.000 |
| Benzophenone | 119-61-9 | 23.000 |
| Vertofix Coeur | 32388-55-9 | 3.000 |
| Helional | 1205-17-0 | 2.000 |
| Methyl Palmitate | 112-39-0 | 20.000 |
| Vetivert Acetate | 117-98-6 | 0.5 |
| Farnesol | 4602-84-0 | 43.5 |
| Styrax Coeur | 8046-19-3 | 4.5 |

In some embodiments, the malodor control composition includes a mixture of perfume materials identified in Tables 1-3 along with a mixture of two or more volatile aldehydes selected from the group consisting of 2-ethoxy Benzylaldehyde, 2-isopropyl-5-methyl-2-hexenal, 5, -methyl Furfural, 5-methyl-thiophene-carboxaldehyde, p-anisaldehyde, Benzylaldehyde, Cinnamic aldehyde, Decyl aldehyde, Ligustral, Lyral, Melonal, o-anisaldehyde, P.T. Bucinal, Thiophene carboxaldehyde (TC), trans-4-Decenal, trans trans 2,4-Nonadienal, Undecyl aldehyde, and mixtures thereof.

In some embodiments, the perfume mixture includes the volatile aldehyde mixture shown in Table 4 and referred to herein as Accord A.

TABLE 4

Accord A

| Material | Wt. % (of the volatile aldehydes in the perfume mixture) | CAS Number | ClogP Group | VP(torr) @25° C. |
|---|---|---|---|---|
| Intreleven Aldehyde | 5.000 | 112-45-8 | 3 | 0.060 |
| Florhydral | 10.000 | 125109-85-5 | 4 | 0.008 |
| Floral Super | 25.000 | 71077-31-1 | 3 | 0.030 |
| Scentenal | 10.000 | 86803-90-9 | 2 | 0.010 |
| Cymal | 25.000 | 103-95-7 | 4 | 0.007 |
| o-anisaldehyde | 25.000 | 135-02-4 | 1 | 0.032 |

In another embodiment, the perfume mixture includes the volatile aldehyde mixture showin in Table 5 and referred to herein as Accord B.

TABLE 5

Accord B

| Material | Wt. % (of the volatile aldehydes in the perfume mixture) | CAS Number | ClogP Group | VP (torr) @25° C. |
|---|---|---|---|---|
| Intreleven Aldehyde | 2.000 | 112-45-8 | 3 | 0.060 |
| Florhydral | 20.000 | 125109-85-5 | 4 | 0.008 |
| Floral Super | 10.000 | 71077-31-1 | 3 | 0.030 |
| Scentenal | 5.000 | 86803-90-9 | 2 | 0.010 |
| Cymal | 25.000 | 103-95-7 | 4 | 0.007 |
| Floralozone | 10.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| o-anisaldehyde | 25.000 | 135-02-4 | 1 | 0.032 |

In another embodiment, the perfume mixture includes the volatile aldehyde mixture shown in Table 6 and referred to herein as Accord C.

TABLE 6

Accord C

| Material | Wt. % (of the volatile aldehydes in the perfume mixture) | CAS Number | ClogP Group | VP (torr) @25° C. |
|---|---|---|---|---|
| Intreleven Aldehyde | 2.000 | 112-45-8 | 3 | 0.060 |
| Florhydral | 10.000 | 125109-85-5 | 4 | 0.008 |
| Floral Super | 5.000 | 71077-31-1 | 3 | 0.030 |
| Scentenal | 2.000 | 86803-90-9 | 2 | 0.010 |
| Cymal | 15.000 | 103-95-7 | 4 | 0.007 |
| Floralozone | 12.000 | 67634-14-4 | 4 | 0.005 |
| Adoxal | 1.000 | 141-13-9 | 4 | 0.007 |
| Methyl Nonyl Acetaldehyde | 1.000 | 110-41-8 | 3 | 0.030 |
| Melonal | 1.000 | 106-72-9 | 3 | 0.670 |
| Flor Acetate | 11.800 | 5413-60-5 | 1 | 0.060 |
| Frutene | 7.000 | 17511-60-3 | 4 | 0.020 |
| Helional | 5.000 | 1205-17-0 | 2 | 0.0005 |
| Bourgeonal | 2.000 | 18127-01-0 | 4 | 0.004 |
| Linalool | 10.000 | 78-70-6 | 3 | 0.050 |
| Benzaldehyde | 0.200 | 100-52-7 | 1 | 1.110 |
| o-anisaldehyde | 15.000 | 135-02-4 | 1 | 0.320 |

Accords A, B, or C can be formulated in with the perfume mixture outlined in Tables 1 to 3 or with any other unscented or low scented perfume materials in an amount of about 5% to about 50%, alternatively about 5% to about 40%, alternatively about 5% to about 30%, alternatively about 5% to about 20%, alternatively about 5% to about 10%, by weight of the perfume mixture.

The unscented or low scented perfume mixture may be present in an amount up to 100%, by weight of the malodor control composition, alternatively from about 5% to about 100%, alternatively from about 10% to about 100%, alternatively from about 30% to about 100%, alternatively from about 50% to about 100%, alternatively from about 70% to about 100%, alternatively from about 80% to about 100%, alternatively from about 0.001% to about 5%, alternatively from about 0.001% to about 2%, alternatively from about 0.001% to about 0.5%, alternatively from about 0.001% to about 0.3%, alternatively from about 0.001% to about 0.1%, alternatively about 0.001%, by weight of the composition.

In some embodiments where volatility is not important for neutralizing a malodor, the present invention may include poly-aldehydes, for example, di-, tri-, tetra-aldehydes. Such embodiments may include laundry detergents, additive, and the like for leave-on, through the wash, and rinse-off type of applications.

2. Acid Catalyst

The malodor control compositions of the present invention may include an effective amount of an acid catalyst to neutralize sulfur-based malodors. It has been found that certain mild acids have an impact on aldehyde reactivity with thiols in the liquid and vapor phase. It has been found that the reaction between thiol and aldehyde is a catalytic reaction that follows the mechanism of hemiacetal and acetal formation path. When the present malodor control composition contains an acid catalyst and contacts a sulfur-based malodor, volatile aldehydes react with thiol. This reaction may form a thiol acetal compound, thus, neutralizing the sulfur-based odor. Without an acid catalyst, only hemi-thiol acetal is formed.

Suitable acid catalysts have a VP, as reported by Scifinder, in the range of about 0.001 torr to about 38 torr, alternatively about 0.001 torr to about 14 torr, alternatively from about 0.001 to about 1, alternatively from about 0.001 to about 0.020, alternatively about 0.005 to about 0.020, alternatively about 0.010 to about 0.020, measured at 25° C.

The acid catalyst may be a weak acid. A weak acid is characterized by an acid dissociation constant, $K_a$, which is an equilibrium constant for the dissociation of a weak acid; the pKa being equal to minus the decimal logarithm of $K_a$. The acid catalyst may have a pKa from about 4.0 to about 6.0, alternatively from about 4.3 and 5.7, alternatively from about 4.5 to about 5, alternatively from about 4.7 to about 4.9. Suitable acid catalysts include those listed in Table 7.

TABLE 7

| Acid | VP (torr) @25° C. |
|---|---|
| Formic Acid | 36.5 |
| Acetic Acid | 13.9 |
| Trimethyl Acetic Acid | 0.907 |
| Phenol (alkaline in liquid apps yet acidic in vapor phase) | 0.610 |
| Tiglic acid | 0.152 |
| Caprylic acid | 0.0222 |
| 5-Methyl thiophene carboxylic acid | 0.019 |
| Succinic acid | 0.0165 |
| Benzoic acid | 0.014 |
| Mesitylenic acid | 0.00211 |

In some embodiments, it may be desirable to select an acid catalyst that provides a neutral scent. Such acid catalysts may have a VP of about 0.001 torr to about 0.020 torr, measured at 25° C., alternatively about 0.005 torr to about 0.020 torr, alternatively about 0.010 torr to about 0.020 torr. Non-limiting examples of such acid catalyst include succinic acid and benzoic acid.

The malodor control composition may include about 0.05% to about 5%, alternatively about 0.1% to about 1.0%, alternatively about 0.1% to about 0.5%, alternatively about 0.1% to about 0.4%, alternatively about 0.4% to about 1.5%, alternatively about 0.4% of an acid catalyst, by weight of the malodor control composition.

In an acetic acid system, the present malodor control composition may include about 0.4% of acetic acid (50:50 thiophene carboxaldehye (TC): dipropylene glycol methyl ether (DPM), 0.4% acetic acid).

TABLE 8

| Sample Formulated | Actual % acetic acid in DPM | % Butanethiol reduction @ 30 min. |
|---|---|---|
| 50:50 TC:DPM 0% Acetic Acid | 0.00 | 12.00 |
| 50:50 TC:DPM 0.05% Acetic Acid | 0.04 | 14.65 |
| 50:50 TC:DPM 0.1% Acetic Acid | 0.10 | 25.66 |
| 50:50 TC:DPM 0.2% Acetic Acid | 0.42 | 34.68 |
| 50:50 TC:DPM 0.5% Acetic Acid | 1.00 | 24.79 |
| 50:50 TC:DPM 1.0% Acetic Acid | 2.00 | 7.26 |

When an acid catalyst is present with a volatile aldehyde, the acid catalyst may increase the efficacy of the volatile aldehyde on malodors in comparison to the malodor efficacy of the volatile aldehyde on its own. For example, 1% volatile aldehyde and 1.5% benzoic acid provides malodor removal benefit equal to or better than 5% volatile aldehyde alone.

The malodor control composition may have a pH from about 3 to about 8, alternatively from about 4 to about 7, alternatively from about, alternatively from about 4 to about 6.

3. Optional Ingredients

The malodor control composition may, optionally, include odor masking agents and/or diluents.

Water and surfactants may also be present in any amount for the composition to make an aqueous solution. In some embodiments, water may be present in an amount of about 85% to 99.5%, alternatively about 90% to about 99.5%, alternatively about 92% to about 99.5%, alternatively about 95%, by weight of said malodor control composition. Water containing a small amount of low molecular weight monohydric alcohols, e.g., ethanol, methanol, and isopropanol, or polyols, such as ethylene glycol and propylene glycol, can also be useful.

The malodor control composition may also comprise 100% of an unscented or low scented perfume mixture according to the present invention.

Exemplary diluents include DPM, and 3-methoxy-3-methyl-1-butanol, and mixtures thereof.

II. Methods of Use

The malodor control composition of the present invention may be used in a wide variety of applications that neutralize malodors in the vapor and/or liquid phase. In some embodiments, the malodor control composition may be formulated for use in non-energized vapor phase systems. "Non-energized" as used herein refers to a system that emits a targeted active passively or without the need for an electrical energy source. Aerosol sprayers and traditional trigger/pump sprayers are considered non-energized systems. For such non-energized systems, the VP of the volatile aldehydes may be about 0.01 torr to about 20 torr, alternatively about 0.05 torr to about 10 torr, measured at 25° C. Non-limiting examples of a non-energized vapor phase system are passive air freshening diffusers such as those known by the trade name Renuzit® Crystal Elements; and aerosol sprays such as fabric and air freshening sprays and body deodorants.

In other embodiments, the malodor control composition may be formulated for use in a liquid phase system. For such systems, the VP may be about 0 torr to about 20 torr, alternatively about 0.0001 torr to about 10 torr, measured at 25° C. Non-limiting examples of a liquid phase system are liquid laundry products, such as laundry detergents and additives; dish detergents; personal hygiene products such as body washes, shampoos, conditioners.

The malodor control composition may also be loaded onto or into known substrates according to known methods. Suitable substrates may include wovens and non-wovens (e.g cellulose fibers for paper products, sponges, and the like). Such substrates may be used to manufacture diapers; baby wipes; adult incontinence products; feminine hygiene products such as sanitary napkins and tampons; cleaning wands for toilets; pet food packaging; paper towels; facial tissues; and the like.

Suitable substrates may also include commercially available films including low density polyethylene (LDPE), linear LDPE (LLDPE), high density polyethylene, plastomers, elastomers, ethylene vinyl acetate, ethyl methacrylates, polymethylpentene copolymers, polyisobutylenes, polyolefin isomers, cyclic olefin copolymers, polyethylene, polypropylene, poly lactic acid based films, polyhydroxy alcohol based films, polyhydroxy butyrate/valerate, polyesters, thermoplastic starch, and combinations thereof. These plastic films may be used to manufacture non-disposable composting containers, trash bags, storage bags, and the like. The malodor control composition may also be used in connection with commercial or industrial septic tanks or sewage treatment equipment.

EXAMPLES

Analytical Test—Effect of Volatile Aldehydes on Amine-based and Sulfur-based Malodors Malodor standards are prepared by pipeting 1 mL of n-butylamine (amine-based malodor) or 1-butanethiol (sulfur-based malodor) into a 1.2 liter gas sampling bag. The bag is then filled to volume with nitrogen and allowed to sit for at least 12 hours to equilibrate.

A 1 µL sample of each volatile aldehyde listed in Table 9 and of each Accord (A, B, and C) listed in Tables 4 to 6 is pipeted into individual 10 mL silanized headspace vials. The vials are sealed and allowed to equilibrate for at least 12 hours. Repeat 4 times for each sample (2 for butylamine analysis and 2 for butanethiol analysis).

After the equilibration period, 1.5 mL of the target malodor standard is injected into each 10 mL vial. For thiol analysis, the vials containing a sample +malodor standard are held at room temperature for 30 minutes. Then, a 1 mL headspace syringe is then used to inject 250 µL of each sample/thiol malodor into a GC/MS split/splitless inlet. For amine analysis, a 1 mL headspace syringe is used to inject 500 µL of each sample/amine malodor immediately into the GC/MS split/splitless inlet. A GC pillow is used for the amine analysis to shorten the run times. Samples are then analyzed using a GC/MS with a DB-5, 20 m, 1 µm film thickness column with an MPS-2 autosampler equipment with static headspace function. Data is analyzed by ion extraction on each total ion current (56 for thiol and 30 for amine) and the area is used to calculate the percent reduction from the malodor standard for each sample.

Table 9 shows the effect of certain volatile aldehydes on neutralizing amine-based and sulfur based malodors at 40 seconds and 30 minutes, respectively.

TABLE 9

| Perfume Raw Material (R—CHO) | At least 20% butylamine reduction at 40 secs.? | At least 20% butanethiol reduction at 30 mins.? |
|---|---|---|
| 2-ethoxy benzylaldehyde | Yes | Yes |
| 2-isopropyl-5-methyl-2-hexenal | Yes | Yes |
| Adoxal | Yes | No |
| Cinnamic aldehyde | Yes | Yes |
| Floral Super | Yes | Yes |
| Florhydral | Yes | Yes |
| o-anisaldehyde | Yes | Yes |
| Pino acetaldehyde | Yes | Yes |
| Trans-4-decenal | Yes | Yes |

Table 10 shows the percent reduction of butylamine and butaniethiol at 40 seconds and 30 minutes, respectively, for Accords A, B, and C.

TABLE 10

| Accord | % reduction of butylamine at 40 secs. | % reduction of butanethiol at 30 mins. |
|---|---|---|
| Accord A | 76.58 | 25.22 |
| Accord B | 51.54 | 35.38 |
| Accord C | 65.34 | 24.98 |

Analytical Test—Effect of Acid Catalysts on Sulfur-based Malodors

The above analytical test is repeated using samples containing an acid catalyst to test their effect on sulfur-based malodors. Specifically, a 1 µL aliquot of each of the following controls and acid catalyst samples are pipeted into individual 10 mL silanized headspace vials in duplicate: TC as a control; a 50/50 mixture of TC and each of the following acid catalysts at 0.04%, 0.10%, 0.43% in DPM, 1.02% in DPM, and 2.04% in DPM: phenol, mesitylenic acid, caprylic acid, succinic acid, pivalic acid, tiglic acid, and benzoic acid.

FIG. 1 demonstrates that low vapor pressure acid catalysts provide up to 3 times better reduction of sulfur-based malodors in comparison to the control.

Analytical Test—Effect of Volatile Aldehydes and Acid Catalyst on Amine-based and Sulfur-based Malodors The above analytical test is repeated using sample formulations containing volatile aldehydes from Accords A, B, and C, in accordance with the present invention, and an acid catalyst, as outlined in Tables 11 and 12.

Tables 11 and 12 show that a perfume mixture having as little as 1% volatile aldehyde along with 1.5% acid catalyst performs better at reducing butylamine and butanethiol than the same perfume mixture having 5% volatile aldehyde.

TABLE 11

| Formulation | % butylamine reduction at 40 secs. | | % butanethiol reduction at 30 mins. | |
|---|---|---|---|---|
| Perfume Mixture w/5% RA (Control) | 34 | — | 2 | — |
| Perfume Mixture w/1% RA and w/1.5% Benzoic Acid | 42 | +7 | 12 | +10 |
| Perfume Mixture w/3% RA and w/1.5% Benzoic Acid | 36 | +2 | 14 | +11 |
| Perfume A Mixture w/5% RA and w/1.5% Benzoic Acid | 41 | +7 | 10 | +5 |

TABLE 12

| Formulation | % butylamine Reduction at 40 secs. | | % butanethiol reduction at 30 mins. | |
|---|---|---|---|---|
| Perfume mixture w/5% RA (Control) | 4.94 | — | 10.52 | — |
| Perfume mixture w/1% RA and w/1.5% Benzoic Acid | 11.61 | +6.67 | 18.82 | +8.30 |
| Perfume mixture w/3% RA and w/1.5% Benzoic Acid | 26.89 | +21.95 | 14.85 | +4.33 |
| Perfume mixture w/5% RA and w/1.5% Benzoic Acid | 20.27 | +15.33 | 16.84 | +6.32 |

Sensory Test—Effect on Sulfur-Based Malodors Technical Olfactive Assessments (TOA) were conducted using passive dispenser devices for the malodor control composition (MCC) perfume oils. Malodors used were either garlic or Ocean Perch fish. Perfume oils tested were "Test MCC" and "Control MCC" as shown in Table 13. The passive dispenser devices were open, circular containers. Different device diameters were used as outlined in Table 14 in order to achieve approximately the same perfume % weight loss rate for the Test and Control MCCs. This is consistent with the molecular diffusion principles outlined on pages 22-34 in the text, *Mass Transfer Operations*, third edition, by Robert E. Treybal.

TABLE 13

| Test MCC | | Control MCC | | |
|---|---|---|---|---|
| Perfume Materials | Wt % (by wt of perfume mixture | Perfume Materials | CAS# | Wt % (by wt of perfume mixture |
| Benzophenone | 27.00% | Fleuramone | 137-03-1 | 27.00% |
| Cedryl methyl ether | 0.50% | Phenyl Ethyl Isoamyl Ether (aka Anther) | 56011-02-0 | 0.50% |
| Florhydral | 1.00% | Nonyl Aldehyde | 124-19-6 | 1.00% |
| Helional | 1.00% | Nonyl aldehyde | 124-19-6 | 1.00% |
| Methyl cedrylone (Vertofix Coeur) | 3.80% | Ethyl Amyl Ketone | 106-68-3 | 3.80% |
| Undecylenic Aldehyde | 0.20% | Laurie Aldehyde | 112-54-9 | 0.20% |
| Methyl Palmitate | 25.00% | Benzyl cinnamate | 103-41-3 | 25.00% |
| Vetivert Acetate | 0.50% | Cis 3 Hexenyl Acetate | 3681-71-8 | 0.50% |
| Farnesol | 40.00% | Laevo Trisandol | 28219-61-6 | 40.00% |
| Adoxal | 1.00% | Citronellyl Oxyacetaldehyde | 7492-67-3 | 1.00% |
| TOTALS | 100.00% | TOTALS | | 100.00% |

TABLE 14

|  | Test MCC | Control MCC |
|---|---|---|
| Passive device diameter (mm) | 86 | 22 |
| Average % weight loss rate (60 min) | 0.25 | 0.26 |

Sensory Test—Effect on a Sulfur-based Malodor, and in-use Scent Level

Place Presto™ skillet into fume hood and turn on to 250° F. Place 80 grams of Crisco® oil into skillet and cover with skillet lid. Allow 10 minutes for equilibration. Remove skillet lid and check oil temperature with thermometer. Place 50 grams of chopped, commercially prepared garlic in water into skillet. Cover skillet with lid. Cook for 2.5 minutes or until garlic is translucent, with a portion staring to turn brown but not burn. Remove garlic from the skillet. Place 5 grams of garlic in each of 3 Petri dishes. Place covers on each Petri dish.

Fill both Test and Control passive dispenser devices with sufficient Test MCC, shown in Table 13, to ensure surface area remains wet throughout test. 5 minutes before cooked garlic is introduced to the test chambers, place each passive dispenser device into individual test chambers on the opposite side of the fan. Each test chamber is 39.25 inches wide, by 25 inches deep, by 21.5 inches high with a volume of 12.2 cubic feet (0.34 cubic meters). The test chamber can be purchased from Electro-Tech Systems, Glenside, Pa. Each test chamber is equipped with a fan (Newark catalog #70K9932, 115 VAC, 90CFM) purchased from Newark Electronics, Chicago, Ill.

Place each covered Petri dish, with 5 grams of garlic, into an individual test chamber in front of the fan. Note: One test chamber will not contain a passive dispenser device. Remove the lids of the Petri dishes to expose contents for a dwell time sufficient to provide an initial odor intensity grade of 70-80 (about 2 minutes). Once the initial odor intensity grade has been reached in a test chamber, remove the Petri dish from the test chamber.

At pre-determined time intervals, trained evaluators open each chamber, smell the chamber for odor intensity, and assign a score for Malodor Intensity, based on the scale in Table 15. Immediately following, the trained evaluator smells the same chamber for perfume scent intensity, and assigns a score for scent intensity, based on the scale in Table 15. The chamber door is closed between sequential evaluators. The scores are tabulated and the average malodor intensity and scent intensity scores for each time interval are recorded.

TABLE 15

Expert Sensory Grader Odor Evaluation Scale

| Score | Description corresponding to Score |
|---|---|
| 0 | No odor present |
| 10 | Very slight odor - "I think there is an odor present" |
| 20 | Slight odor - "I detect something but cannot identify specific odor |
| 25 | Slight odor |
| 50 | Moderate |
| 75 | Strong odor |
| 100 | Extremely Strong odor |

Table 16 demonstrates that the unscented or low scented MCC test mixture according to the present invention provides similar malodor control as the Control MCC perfume mixture but, notably, has less perfume scent intensity.

TABLE 16

|  |  | Malodor Intensity | | Scent Intensity | |
|---|---|---|---|---|---|
| Minutes | Garlic | Test MCC | Control MCC | Test MCC | Control MCC |
| 5 | 80 | 58 | 48 | 42 | 57 |
| 30 | 73 | 40 | 38 | 47 | 53 |
| 60 | 70 | 33 | 31 | 29 | 55 |

Sensory Test—Effect on Amine-based Malodors, and in-use Scent Level

The above sensory protocol was repeated with an amine-based malodor (i.e. Ocean Perch fish).

Separate fresh Ocean Perch fillets from skin and add to a Magic Bullet™ food chopper. Fish meat is chopped for 35-40 seconds. 25 grams of chopped fish is weighed and fashioned into a patty suitable to fit into a 60×15 mm Petri dish. Repeat 2 more times so there is one fish patty in each of 3 Petri dishes. Add 40 g of Crisco® oil to Presto™ skillet. Place lid on skillet and turn on to 350° F. Allow 10 minutes for equilibration. Remove lid. Cut a slit in the middle of each patty, place all patties into skillet, and begin frying. Replace lid. After 2.5 minutes, flip fish patties and fry an additional 2.5 minutes. Remove fish patties from skillet and blot briefly onto a paper towel for 10 seconds. Place each fish patty into a 60×15 mm Petri dish and cover with a lid.

Fill both Test and Control passive dispenser devices with sufficient Test MCC, shown in Table 13, to ensure surface area remains wet throughout test. 5 minutes before cooked ocean perch is introduced to the test chambers, place each passive dispenser device into individual test chambers on the opposite side of the fan.

Introduce each Petri dish containing a fish patty into an individual test chamber in front of the fan. One test chamber will not contain a passive dispenser device. The specifications of the test chamber are the same as those in the above sulfur-based (i.e. garlic) malodor test. Remove the lids to expose contents for a dwell time sufficient to provide an initial odor intensity grade of 70-80 (about 2 minutes). Once the initial odor intensity grade has been reached in a test chamber, remove the Petri dish from the test chamber.

At pre-determined time intervals, trained evaluators open each chamber, smell the chamber for odor intensity, and assign a score for malodor intensity, based on the scale in Table Immediately following, the trained evaluator smells the same chamber for scent intensity, and assigns a score for scent intensity, based on the scale in Table 15. The chamber door is closed between sequential evaluators. The scores are tabulated and the average malodor intensity and scent intensity scores for each time interval are recorded.

Table 17 demonstrates that the unscented or low scented perfume mixture according to the present invention provides similar malodor control as the Control perfume mixture but, notably, has less perfume scent intensity.

TABLE 17

|  |  | Malodor Intensity | | Scent Intensity | |
|---|---|---|---|---|---|
| Minutes | Fish | Test MCC | Control MCC | Test MCC | Control MCC |
| 5 | 81 | 59 | 48 | 21 | 43 |
| 30 | 75 | 34 | 31 | 20 | 40 |
| 60 | 75 | 29 | 24 | 19 | 45 |

Sensory Test—Initial Scent Intensity of Various MCC Loading Levels in Trash Bags The Test MCC formula listed in Table 13 is loaded into plastic trash bag film, according to known methods, at a target loading level. A trained evaluator is given a folded trash bag sample containing the composition at the target loading level. The evaluator grasps the sample with both hands, one hand grabbing each side edge of the bag opening. Evaluator proceeds to open the bag sample by unfolding it, and then shaking it up and down until the bag has been fully opened. Once opened, the evaluator places the opened bag into a clean, appropriate size trash can (e.g. a tall kitchen trash can) and folds the top edge of the open bag over the outer lip of the trash can to secure the bag in place. Once the bag is secured, the evaluator bends down over the trash can and places both arms down into the opened sample until their nose is directly above the opening of the bag and can. The evaluator then moves their arms around inside the bag, stirring up the airspace and keeping their nose in the same area above the bag opening (as if the evaluator were trying to get the air out between the side walls of the bag and the sides of the trash can). The evaluator takes one or more sniffs of the bag headspace air while in this position and performing this step.

After 10 seconds, the evaluator stands up and steps away from the can, and evaluates the intensity of the scent of the Test MCC in the bag following the scale on Table 15.

The above protocol is repeated for each sample and for Test MCC loading level to be evaluated. Evaluator is to allow at least 10 minutes between sample evaluations to clear his/her nose of any residual scent from the previous sample.

Figure 2:
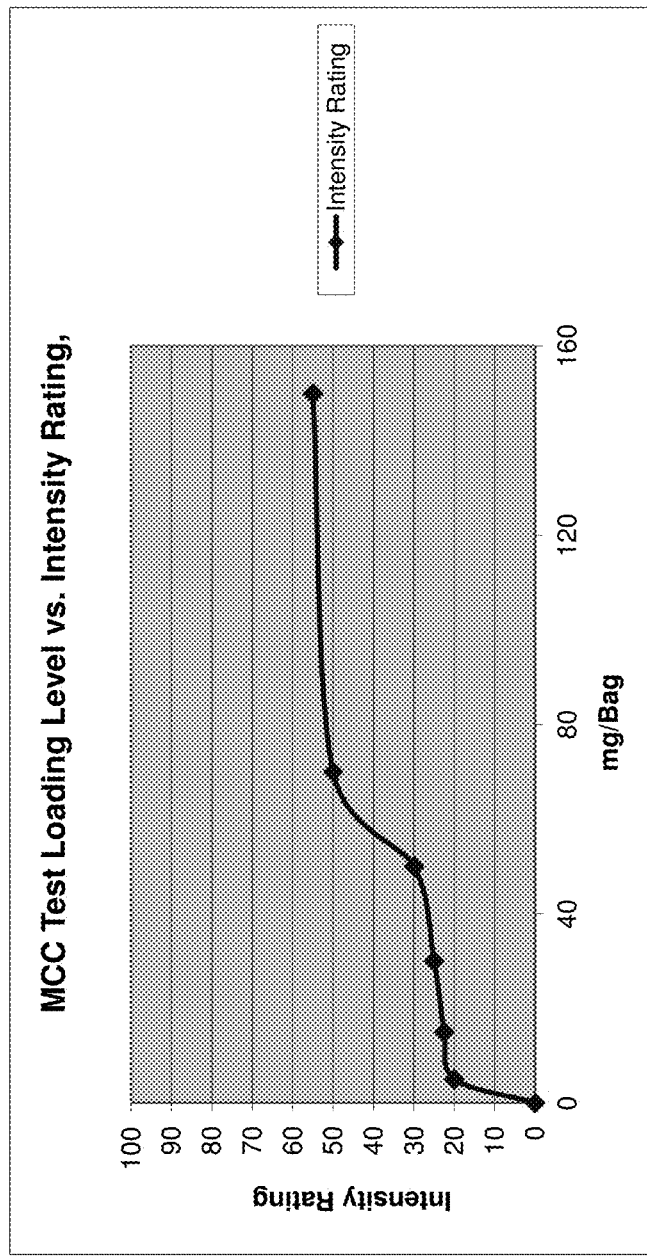
FIG. 2 is a graph showing scent intensities of varying loads of a malodor control composition, in accordance with the present invention, in trash bags.

Table 18 and FIG. 2 show that the perfume intensity rating surprisingly increases less than the incremental increase in the Test MCC loading level seen between 5 and 30 mg.

TABLE 18

| Mg of MCC in bag | Intensity Rating |
|---|---|
| 0 | 0 |
| 5 | 20 |
| 15 | 22.5 |
| 30 | 25 |
| 50 | 30 |
| 70 | 50 |
| 150 | 55 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed:

1. A malodor control composition comprising:
   a perfume mixture comprising benzophenone, methyl palmitate, farnesol, vetivert acetate, and undecylenic aldehyde for reducing malodors.

2. The malodor control composition of claim 1 further comprising cedryl methyl ether, florhydral, helional, vertofix couer, and mixtures thereof.

3. The malodor control composition of claim 1 wherein said perfume mixture further comprises at least one volatile aldehyde selected from the group consisting of floral super, 2-ethoxy Benzylaldehyde, 2-isopropyl-5-methyl-2-hexenal, 5-methyl Furfural, 5-methyl-thiophene-carboxaldehyde, p-anisaldehyde, Benzylaldehyde, Cinnamic aldehyde, Decyl aldehyde, Ligustral, Lyral, Melonal, o-anisaldehyde, P.T. Bucinal, Thiophene carboxaldehyde, trans-4-Decenal, trans trans 2,4-Nonadienal, Undecyl aldehyde, and mixtures thereof.

4. The malodor control composition of claim 1 wherein said perfume mixture further comprises a volatile aldehyde mixture selected from the group consisting of:
   intreleven aldehyde, florhydral, floral super, scentenal, cymal, and o-anisaldehyde (Accord A),
   intreleven aldehyde, florhydral, floral super, scentenal, cymal, floralozone, adoxal, methyl nonyl acetaldehyde, melonal, and o-anisaldehyde (Accord B),
   intreleven aldehyde, florhydral, floral super, scentenal, cymal, floralozone, adoxal, methyl nonyl acetaldehyde, melonal, flor acetate, frutene, helional, bourgeonal, linalool, benzaldehyde, and o-anisaldehyde (Accord C),
   and mixtures thereof.

5. The malodor control composition of claim 4 wherein said perfume mixture further comprises about 1% to about 10% of Accord A, by weight of said perfume mixture.

6. The malodor control composition of claim 1 wherein said perfume mixture is present in an amount from about 50% to about 100%, by weight of said malodor control composition.

7. The malodor control composition of claim 1 further comprising an acid catalyst present in an amount of about 0.1% to about 1.5%, by weight of said malodor control composition.

8. The malodor control composition of claim 7 wherein said acid catalyst has a vapor pressure of about 0.01 to about 2 torr at 25° C.

9. The malodor control composition of claim 7 wherein said acid catalyst is a carboxylic acid.

10. The malodor control composition of claim 9 wherein said acid catalyst is 5-methyl thiophene carboxylic acid.

11. The malodor control composition of claim 1 wherein said composition has a pH of about 4 to about 6.5.

12. The malodor control composition of claim 1 further comprising an ingredient selected from the group consisting of: odor masking agents, odor blocking agents, diluents, and mixtures thereof.

13. A plastic film comprising a perfume mixture comprising benzophenone, undecylenic aldehyde, methyl palmitate, vetivert acetate, farnesol, wherein said perfume mixture reduces malodors in the air.

14. The plastic film of claim 13 wherein said plastic film is LLDPE.

15. The plastic film of claim 13 wherein said plastic film comprises about 0.5 mg to about 50 mg of said perfume mixture.

16. The plastic film of claim 13 wherein said perfume mixture is present in the amount of about 5 mg to about 30 mg.

17. The plastic film of claim 13 wherein said perfume mixture is present in the amount of about 5 mg to about 15 mg.

18. A method of controlling malodors and providing a low scented composition comprising:
   providing the composition of claim 1; and
   contacting said composition with a malodor.

19. The method of claim 18 wherein said contacting step comprises about 5 mg to about 15 mg of said composition.

* * * * *